United States Patent
Pomilla

(10) Patent No.: US 11,419,911 B2
(45) Date of Patent: Aug. 23, 2022

(54) PAIN-RELIEVING COMPOSITION

(71) Applicant: NY Prostyle Beauty LLC, Thornwood, NY (US)

(72) Inventor: Rosemarie Pomilla, Thornwood, NY (US)

(73) Assignee: NY Prostyle Beauty LLC, Thornwood, NY (US)

( * ) Notice: Subject to any disclaimer, the term of this patent is extended or adjusted under 35 U.S.C. 154(b) by 0 days.

(21) Appl. No.: 16/559,193

(22) Filed: Sep. 3, 2019

(65) Prior Publication Data

US 2021/0060113 A1 Mar. 4, 2021

(51) Int. Cl.
| | |
|---|---|
| *A61K 36/889* | (2006.01) |
| *A61K 9/00* | (2006.01) |
| *A61K 35/644* | (2015.01) |
| *A61K 36/53* | (2006.01) |

(52) U.S. Cl.
CPC .......... *A61K 36/889* (2013.01); *A61K 9/0014* (2013.01); *A61K 35/644* (2013.01); *A61K 36/53* (2013.01)

(58) Field of Classification Search
None
See application file for complete search history.

(56) References Cited

U.S. PATENT DOCUMENTS

| | | | |
|---|---|---|---|
| 7,029,711 B2 | 4/2006 | Farrell | |
| 9,801,926 B2 | 10/2017 | Lannes et al. | |
| 2008/0145461 A1 | 6/2008 | Gonzalez | |
| 2009/0123504 A1 | 5/2009 | Feldkamp et al. | |
| 2011/0142954 A1 | 6/2011 | Koelzer et al. | |
| 2014/0127315 A1* | 5/2014 | Brown | A61K 31/20 424/539 |
| 2015/0328222 A1 | 11/2015 | Tortoriello et al. | |
| 2017/0056465 A1 | 3/2017 | Tobin et al. | |

FOREIGN PATENT DOCUMENTS

EP 0923935 A1 6/1999

OTHER PUBLICATIONS

Website document entitled: "Easy 3 ingredient diy peppermint lip balm" (available at www.livingwellmom.com/easy-3-ingredient-diy-peppermint-lip-balm). Downloaded Apr. 4, 2021. (Year: 2016).*
Website document entitled "Homemade Eucalyptus Lip Balm-Amazing Cooling Effect" (available at sweetnaturesbeauty.com/homemade-eucalyptus-lip-balm). Archived to Nov. 20, 2017. (Year: 2017).*
Onegoodthingbyjillee, "Soothe Aches And Pains With This Easy-To-Make Cream", http://www.onegoodthingbyjillee.com/homemade-pain-relieving-cream, Mar. 13, 2018.
Modernalternativemama, "Homemade Pain Cream", http://www.modernaltemativemama.com/2013/01/08/homemade-pain-cream, Jan. 3, 2018.
Good Housekeeping "Make This DIY Muscle Soothing Rub At Home With Just 4 Ingredients", http://www.goodhousekeeping.com/health/wellness/g20706928/diy-muscle-soothing-rub, Apr. 24, 2017.
Dr. Axe, "Homemade Muscle Rub", https://draxe.com/natural-remedy/body-care/homemade-muscle-rub, 2014.
Six Dollar Family, "Homemade Muscle Pain Relief Cream", http://www.sixdollarfamily.com/homemade-muscle-pain-relief-cream, Feb. 11, 2016.

* cited by examiner

*Primary Examiner* — Russell G Fiebig
(74) *Attorney, Agent, or Firm* — Kim IP Law Group LLC

(57) ABSTRACT

A pain-relieving composition for topical administration and processes for preparing and using the same. The pain-relieving composition comprises beeswax, coconut oil, and peppermint essential oil, and, at a minimum, does not comprise dimethylsulfoxide, methylsulfonylmethane, a non-steroidal anti-inflammatory drug, an analgesic, an anesthetic, olecanthal, an olecanthal-related compound, potassium aluminum sulfate, stearic acid, camphor, cayenne, a non-essential oil in addition to the coconut oil, or water; and does not further comprise both *Eucalyptus* essential oil and lavender essential oil. The processes for preparing such pain-relieving compositions comprises providing beeswax, coconut oil, and peppermint essential oil, melting the beeswax and coconut oil to form a molten beeswax and coconut oil mixture, and combining the peppermint essential oil with the molten beeswax and coconut oil mixture.

3 Claims, No Drawings

PAIN-RELIEVING COMPOSITION

FIELD OF THE INVENTION

The present disclosure relates generally to compositions, particularly compositions containing naturally-derived ingredients, capable of providing pain relief to muscles and/or joints via topical application, as well as processes for preparing and using such compositions.

BACKGROUND OF THE INVENTION

Persons suffering from muscular and/or joint pain often treat such pain topically, such as with a cream, ointment, gel, lotion, or spray. For example, persons suffering from muscular and/or joint aches may choose to treat the muscle and/or joint ache by topically applying a rubefacient containing camphor, menthol, and/or methyl salicylate to the skin proximal the aching muscle and/or joint. However, such products typically contain many additional synthetically-derived chemicals in addition to these naturally-derived active ingredients. Products such as these that contain drugs and/or synthetically-derived chemicals can have various side effects and drawbacks which are undesirable for many users. Accordingly, there remains a continuing need for topically applied pain-relieving compositions that do not contain such components.

EMBODIMENTS OF THE INVENTION

This need is met by the pain-relieving compositions according to the present invention, which contain naturally-derived ingredients and provide pain relief to muscles and/or joints when topically applied thereto.

One aspect of the present invention is directed to pain-relieving compositions for topical administration comprising beeswax, coconut oil, and peppermint essential oil, with the proviso that the pain-relieving composition does not comprise dimethylsulfoxide, methylsulfonylmethane, a non-steroidal anti-inflammatory drug, an analgesic, an anesthetic, olecanthal, an olecanthal-related compound, potassium aluminum sulfate, stearic acid, camphor, cayenne, a non-essential oil in addition to the coconut oil, or water, and wherein the pain-relieving composition does not further comprise both *Eucalyptus* essential oil and lavender essential oil.

Another aspect of the present invention is directed to processes for preparing the above pain-relieving compositions according to the present invention comprising the steps of (1) providing beeswax, coconut oil, and peppermint essential oil, (2) melting the beeswax and coconut oil to form a molten beeswax and coconut oil mixture, and (3) combining the peppermint essential oil with the molten beeswax and coconut oil mixture.

In certain embodiments of the above aspects of the present invention, the beeswax, coconut oil, and peppermint essential oil are present in the pain-relieving composition according to the present invention in a ratio by volume in the range of from 1:1:1 to 1:2:2, respectively, relative to the total volume of the pain-relieving composition. In certain other embodiments of the above aspects of the present invention, the beeswax, coconut oil, and peppermint essential oil are present in the pain-relieving composition according to the present invention in a ratio by volume of 3:4:4, respectively, relative to the total volume of the pain-relieving composition.

In certain other embodiments of the above aspects of the present invention, the pain-relieving composition according to the present invention consists essentially of beeswax, coconut oil, and peppermint essential oil. In yet certain other embodiments of the above aspects of the present invention, the pain-relieving composition according to the present invention consists of beeswax, coconut oil, and peppermint essential oil.

The foregoing embodiments are illustrative only and are not intended to be in any way limiting. In addition to the illustrative aspects, embodiments, and features described above, further aspects, embodiments, and features will become apparent by reference to the following detailed description.

DETAILED DESCRIPTION OF THE INVENTION

The illustrative embodiments described in the following detailed description are not meant to be limiting. Other embodiments may be contemplated, and other changes may be made, without departing from the spirit or scope of the subject matter presented here. In the description that follows, a number of terms are used extensively. The terms described below are more fully understood by reference to the specification as a whole.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

According to the first aspect of the present invention, the pain-relieving compositions according to the present invention comprise beeswax, coconut oil, and peppermint essential oil. The pain-relieving compositions according to the present invention, however, do not comprise dimethylsulfoxide, methylsulfonylmethane, a non-steroidal anti-inflammatory drug, an analgesic, an anesthetic, olecanthal, an olecanthal-related compound, potassium aluminum sulfate, stearic acid, camphor, cayenne, a non-essential oil in addition to the coconut oil, or water. Moreover, while the pain-relieving composition according to the present invention may further comprise *Eucalyptus* essential oil or lavender essential oil, it does not further comprise both.

The beeswax component of the pain-relieving compositions according to the present invention can be any suitable beeswax. Examples of such beeswaxes may include, but are not limited to, yellow beeswax, white beeswax, beeswax absolute, and any combination thereof.

The coconut oil component of the pain-relieving compositions according to the present invention can be any suitable food or cosmetic grade coconut oil. Examples of such coconut oils may include, but are not limited to, organic coconut oils, non-organic coconut oils, refined coconut oils, unrefined coconut oils, virgin coconut oils, extra virgin coconut oils, centrifuge extracted coconut oils, cold pressed coconut oils, expeller-pressed coconut oils, raw coconut oils, whole kernel coconut oils, white kernel coconut oils, fractionated coconut oils, hydrogenated coconut oils, medium chain triglyceride (MCT) oils, medium chain fatty acid (MCFA) oils, RBD (refined, bleached, and deodorized) coconut oils, and any combination thereof.

The peppermint essential oil component of the pain-relieving compositions according to the present invention can be any suitable peppermint essential oil. In certain embodiments, such suitable peppermint essential oils can be derived from the species *Mentha piperita*, the species *Mentha haplocalyx*, or any combination thereof.

The pain-relieving compositions according to the present invention do not comprise a non-steroidal anti-inflammatory drug. Examples of such non-steroidal anti-inflammatory drugs include, but are not limited to, ibuprofen, aspirin, difunisal, etodolac, indometacin, nabumeton, sulindac, tolmetin, caprofen, fenbufen, flubiprofen, ketoprofen, ketorolac, loxoprofen, naproxen, oxaprozin, tiaprofenic acid, suprofen, mefenaminic acid, phenylbutazone, piroxicam, meloxicam, celecoxib, etoricoxib, lumiracoxib, parecoxib, rofecoxib, valdecoxib, nimesulide, salts and derivatives of any of these compounds, and combinations thereof.

The pain-relieving compositions according to the present invention do not comprise an analgesic. Examples of such analgesics include, but are not limited to, paracetamol (i.e., acetaminophen), non-steroidal anti-inflammatory drugs, such as those listed above, and opioids, such as morphine, codeine, oxycodone, hydrocodone, dihydromorphine, pethidine, salts and derivatives of any of these compounds, and combinations thereof.

The pain-relieving compositions according to the present invention do not comprise an anesthetic. Examples of such anesthetics include, but are not limited to, pramoxine, lidocaine, benzocaine, prilocaine, lignocaine, xylocaine, bupivacaine, tetracaine, dyclonine, dibucaine, xylocaine, ketocaine, salts and derivatives of any of these compounds, and combinations thereof.

The pain-relieving compositions according to the present invention do not comprise an olecanthal-related compound. Examples of such olecanthal-related compounds include, but are not limited to, those disclosed in U.S. Patent Application Publication No. 2009/0123504 A1, which is incorporated herein by reference in its entirety.

The pain-relieving compositions according to the present invention do not comprise a non-essential oil in addition to the coconut oil. Examples of such non-essential oils may include, but are not limited to edible, vegetable-derived cooking oils, such as olive oil, canola oil, corn oil, palm oil, soybean oil, cottonseed oil, rapeseed oil, safflower oil, sesame oil, sunflower oil, grapeseed oil, avocado oil, castor oil, and peanut oil, edible, animal-derived cooking oils, such as butter, lard, and beef tallow, and combinations thereof.

The beeswax, coconut oil, and peppermint essential oil components of the pain-relieving compositions according to the present invention can be present in the pain-relieving composition in any suitable ratio by volume relative to the total volume of the pain-relieving composition. In certain embodiments, the beeswax, coconut oil, and peppermint essential oil components of the pain-relieving compositions according to the present invention can be present in the pain-relieving composition in a ratio by volume in the range of from 1:1:1 to 1:2:2, respectively, relative to the total volume of the pain-relieving composition. In a particular embodiment, the beeswax, coconut oil, and peppermint essential oil components of the pain-relieving compositions according to the present invention can be present in the pain-relieving composition in a ratio by volume of 3:4:4, respectively, relative to the total volume of the pain-relieving composition.

The pain-relieving compositions according to the present invention may further comprise any suitable additional components, with the exception of dimethylsulfoxide, methylsulfonylmethane, non-steroidal anti-inflammatory drugs, analgesics, anesthetics, olecanthal, olecanthal-related compounds, potassium aluminum sulfate, stearic acid, camphor, cayenne, non-essential oil in addition to the coconut oils, and water. Examples of such suitable additional components may include, but are not limited to, bromelain, aloe vera, glycyrrhicin, papain, tannic acid, cannabidiol, glucosamine, glucosamine salts, glucosamine derivatives, ginger (fresh or dried), turmeric (fresh or dried), shea butter, coconut butter, sal butter, and essential oils, such as lavender oil, chamomile oil, palmarosa oil, jojoba oil, tea tree oil, clary sage oil, cinnamon oil, geranium oil, lemon oil, lime oil, orange oil, sweet orange oil, clove oil, cypress oil, *Arnica* oil, grapefruit oil, rosemary oil, aniseed oil, *Eucalyptus* oil, emu oil, calamus oil, cedarwood oil, citronella oil, sweet birch oil, mint oil, nutmeg oil, vetiver oil, wintergreen oil, ylang-ylang oil, neroli oil, sage oil, sandalwood oil, frankincense oil, slippery elm oil, ginger oil, valerian oil, peppermint oil, wintergreen oil, black pepper oil, jasmine absolute, helichysum oil, spearmint oil, patchouli oil, rosewood oil, vanilla oil, lemongrass oil, basil oil, bergamot oil, balsam oils, tangerine oil, Hinoki oil, Hiba oil, ginko oil, *Eucalyptus* oil, pomegranate oil, manuka oil, calendula oil, and any combination thereof. In certain embodiments, the pain-relieving compositions according to the present invention may further comprise *Eucalyptus* essential oil or lavender essential oil, but not both. In certain other embodiments, the pain-relieving compositions according to the present invention may further comprise ginger or turmeric, but not both. In certain other embodiments, the pain-relieving compositions according to the present invention may further comprise shea butter or coconut butter, but not both.

It should be readily apparent to persons of ordinary skill in the art that above-listed additional components possess well-known properties that, if included in the pain-relieving compositions according to the present invention, may impart those same properties to the pain-relieving compositions according to the present invention, and, thus, may materially affect its basic and novel characteristics. Therefore, in certain embodiments, the pain-relieving compositions according to the present invention do not further comprise bromelain, aloe vera, glycyrrhicin, papain, tannic acid, cannabidiol, glucosamine, glucosamine salts, glucosamine derivatives, ginger (fresh or dried), turmeric (fresh or dried), shea butter, coconut butter, sal butter, and essential oils, such as lavender oil, chamomile oil, palmarosa oil, jojoba oil, tea tree oil, clary sage oil, cinnamon oil, geranium oil, lemon oil, lime oil, orange oil, sweet orange oil, clove oil, cypress oil, *Arnica* oil, grapefruit oil, rosemary oil, aniseed oil, *Eucalyptus* oil, emu oil, calamus oil, cedarwood oil, citronella oil, sweet birch oil, mint oil, nutmeg oil, vetiver oil, wintergreen oil, ylang-ylang oil, neroli oil, sage oil, sandalwood oil, frankincense oil, slippery elm oil, ginger oil, valerian oil, peppermint oil, wintergreen oil, black pepper oil, jasmine absolute, helichysum oil, spearmint oil, patchouli oil, rosewood oil, vanilla oil, lemongrass oil, basil oil, bergamot oil, balsam oils, tangerine oil, Hinoki oil, Hiba oil, ginko oil, *Eucalyptus* oil, pomegranate oil, manuka oil, calendula oil, and any combination thereof. In certain other embodiments, the pain-relieving composition according to the present invention consists essentially of beeswax, coconut oil, and peppermint essential oil. In yet certain other embodiments, the pain-relieving composition according to the present invention consists of beeswax, coconut oil, and peppermint essential oil.

According to the second aspect of the present invention, the pain-relieving compositions according to the present invention are prepared according to a process comprising the steps of (1) providing beeswax, coconut oil, and peppermint essential oil, (2) melting the beeswax and coconut oil to form a molten beeswax and coconut oil mixture, (3) and combining the peppermint essential oil with the molten beeswax and coconut oil mixture. The beeswax and coconut oil can be melted in any suitable manner known in the art. In certain embodiments, the beeswax and coconut oil are melted via gentle heating using a hot water bath or a double boiler. In certain embodiments, the beeswax and coconut oil can be melted separately. In certain other embodiments, the beeswax and coconut oil can be melted together. The peppermint essential oil and any further components can be combined with the molten beeswax and coconut oil mixture and then mixed in any suitable manner in order to form homogenous mixture. The molten mixture of beeswax, coconut oil, and peppermint essential oil and further components, if any, can then poured be into a container and allowed to cool to form a waxy, pain-relieving composition according to the present invention.

The pain-relieving compositions according to the present invention can be used to relieve pain associated muscle and/or joint aches and injuries. The pain-relieving compositions according to the present invention are simply applied directly to the area of skin proximate to the affected area of muscle and/or joint. In certain embodiments, the pain-relieving compositions according to the present invention can be rubbed or massaged into the area of skin proximate to the affected area of muscle and/or joint after application thereto. The pain-relieving compositions according to the present invention can be applied in to the area of skin proximate to the affected area of muscle and/or joint in any suitable amount and with any suitable frequency. In certain embodiments, the pain-relieving compositions according to the present invention can be applied to the area of skin proximate to the affected area of muscle and/or joint once daily. In certain embodiments, the pain-relieving compositions according to the present invention can be applied to the area of skin proximate to the affected area of muscle and/or joint twice daily. In certain embodiments, the pain-relieving compositions according to the present invention can be applied to the area of skin proximate to the affected area of muscle and/or joint three times daily. In certain embodiments, the pain-relieving compositions according to the present invention can be applied to the area of skin proximate to the affected area of muscle and/or joint four times daily. In certain embodiments, the pain-relieving compositions according to the present invention can be applied to the area of skin proximate to the affected area of muscle and/or joint five times daily. In certain embodiments, the pain-relieving compositions according to the present invention can be applied to the area of skin proximate to the affected area of muscle and/or joint as needed.

The foregoing description and the claims will be more readily understood by referring to the following non-limiting example of the present invention, which is given to illustrate a certain specific embodiment thereof rather than limit its scope. While the following non-limiting example illustrate a certain specific embodiment of the present invention, it will be apparent and manifest to, and envisioned by, persons of ordinary skill in the art reading this description that various modifications, rearrangements, changes, and variations may be made thereto without departing from the spirit and scope of the underlying present invention and that the same is not limited to the particular embodiments shown and described herein. In other words, the following example is not intended to be exhaustive in scope, but rather is encompassed within the spirit and scope of the present invention and, thus, the present invention should not be construed as limited to the following embodiment.

EXAMPLE

Beeswax (29.574 mL; 2 tablespoons) and coconut oil (29.574 mL; 2 tablespoons) was placed in a water double boiler and heated until completely melted. The molten mixture of beeswax and coconut oil was removed from the heat and peppermint essential oil (22.181 mL; 1.5 tablespoons) was added thereto. The resulting mixture was stirred thoroughly to achieve homogeneity. The molten mixture of beeswax, coconut oil, and peppermint essential oil was then poured into a container and allowed to cool to form a waxy composition.

The invention claimed is:

1. A topical pain-relieving composition for administration to a subject in need thereof comprising an effective amount of: *Eucalyptus* essential oil, beeswax, coconut oil, and peppermint essential oil, wherein the *Eucalyptus* essential oil, beeswax, coconut oil, and peppermint essential oil are present in the pain-relieving composition in a ratio by volume of 1:18:24:24, respectively.

2. A topical pain-relieving composition for administration to a subject in need thereof consisting essentially of an effective amount of: *Eucalyptus* essential oil, beeswax, coconut oil, and peppermint essential oil, wherein the *Eucalyptus* essential oil, beeswax, coconut oil, and peppermint essential oil are present in the pain-relieving composition in a ratio by volume of 1:18:24:24, respectively.

3. A topical pain-relieving composition for administration to a subject in need thereof consisting of an effective amount of: *Eucalyptus* essential oil, beeswax, coconut oil, and peppermint essential oil, wherein the *Eucalyptus* essential oil, beeswax, coconut oil, and peppermint essential oil are present in the pain-relieving composition in a ratio by volume of 1:18:24:24, respectively.

* * * * *